(12) United States Patent
Gemma et al.

(10) Patent No.: US 10,603,012 B2
(45) Date of Patent: Mar. 31, 2020

(54) PROBE AND INFORMATION ACQUIRING DEVICE

(71) Applicant: CANON KABUSHIKI KAISHA, Tokyo (JP)

(72) Inventors: Naoyo Gemma, Kawasaki (JP); Atsushi Kandori, Ebina (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 871 days.

(21) Appl. No.: 15/089,916

(22) Filed: Apr. 4, 2016

(65) Prior Publication Data
US 2016/0302767 A1   Oct. 20, 2016

(30) Foreign Application Priority Data

Apr. 16, 2015 (JP) .................... 2015-084444

(51) Int. Cl.
*A61B 8/00* (2006.01)
*B06B 1/02* (2006.01)

(52) U.S. Cl.
CPC .......... *A61B 8/4483* (2013.01); *B06B 1/0292* (2013.01)

(58) Field of Classification Search
CPC ............................ A61B 8/4483; B06B 1/0292
See application file for complete search history.

(56) References Cited

U.S. PATENT DOCUMENTS

| | | | |
|---|---|---|---|
| 4,372,323 A * | 2/1983 | Takemura | A61B 8/08 600/447 |
| 7,149,442 B2 | 12/2006 | Ushijima et al. | |
| 7,382,137 B2 | 6/2008 | Ushijima et al. | |
| 7,741,851 B2 | 6/2010 | Ushijima et al. | |
| 8,176,780 B2 | 5/2012 | Takagi et al. | |
| 8,336,380 B2 | 12/2012 | Kandori et al. | |
| 8,339,014 B2 | 12/2012 | Kandori et al. | |
| 8,393,211 B2 | 3/2013 | Kandori et al. | |

(Continued)

FOREIGN PATENT DOCUMENTS

| | | |
|---|---|---|
| JP | 2006-326701 A | 12/2006 |
| JP | 2007-115631 | 5/2007 |

(Continued)

OTHER PUBLICATIONS

Japanese Office Action dated Sep. 28, 2018 during prosecution of related Japanese application No. 2015-084444. (English-language machine translation included.).

*Primary Examiner* — Michael T Rozanski
(74) *Attorney, Agent, or Firm* — Venable LLP

(57) ABSTRACT

In order to provide a technology that does not require, in a probe, provision of a bias voltage storage unit and a communication unit and, in an apparatus main body, provision of a communication unit configured to communicate to/from the probe and a unit configured to control a bias voltage based on a value obtained by the communication, there is provided a probe including a plurality of cells, the cell including a first electrode and a second electrode disposed so as to be opposed to the first electrode across a gap. The plurality of cells include: a first cell configured to perform at least one of transmission or reception of an ultrasound wave; and a second cell in which pull-in occurs at a voltage lower than a pull-in voltage of the first cell and which is configured to be short-circuited at a time of the pull-in.

19 Claims, 4 Drawing Sheets

(56) References Cited

U.S. PATENT DOCUMENTS

| | | | |
|---|---|---|---|
| 8,754,660 B2 | 6/2014 | Kandori et al. | |
| 8,787,117 B2 | 7/2014 | Kandori | |
| 8,928,042 B2 | 1/2015 | Kandori et al. | |
| 8,953,414 B2 | 2/2015 | Kandori | |
| 9,073,085 B2 | 7/2015 | Kandori et al. | |
| 9,089,874 B2 | 7/2015 | Asafusa et al. | |
| 9,101,958 B2 | 8/2015 | Kandori et al. | |
| 9,238,250 B2 | 1/2016 | Kandori et al. | |
| 9,258,650 B2 | 2/2016 | Kandori | |
| 2008/0197751 A1* | 8/2008 | Huang | B06B 1/0292 310/311 |
| 2010/0137719 A1* | 6/2010 | Ikeda | A61B 8/4483 600/459 |
| 2014/0285219 A1 | 9/2014 | Kandori et al. | |
| 2014/0360272 A1 | 12/2014 | Kandori | |
| 2016/0087551 A1 | 3/2016 | Kandori et al. | |

FOREIGN PATENT DOCUMENTS

| | | |
|---|---|---|
| JP | 2011-166632 A | 8/2011 |
| JP | 2013-126069 | 6/2013 |
| JP | 5303472 B2 | 10/2013 |
| WO | 2008/136198 A1 | 11/2008 |

\* cited by examiner

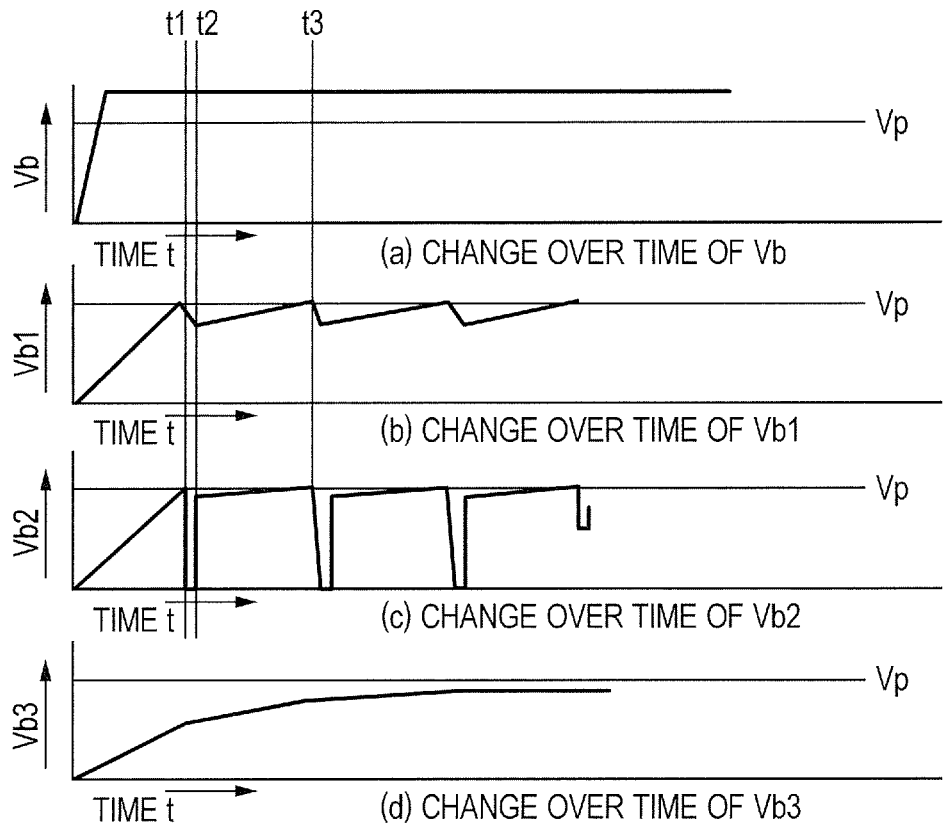
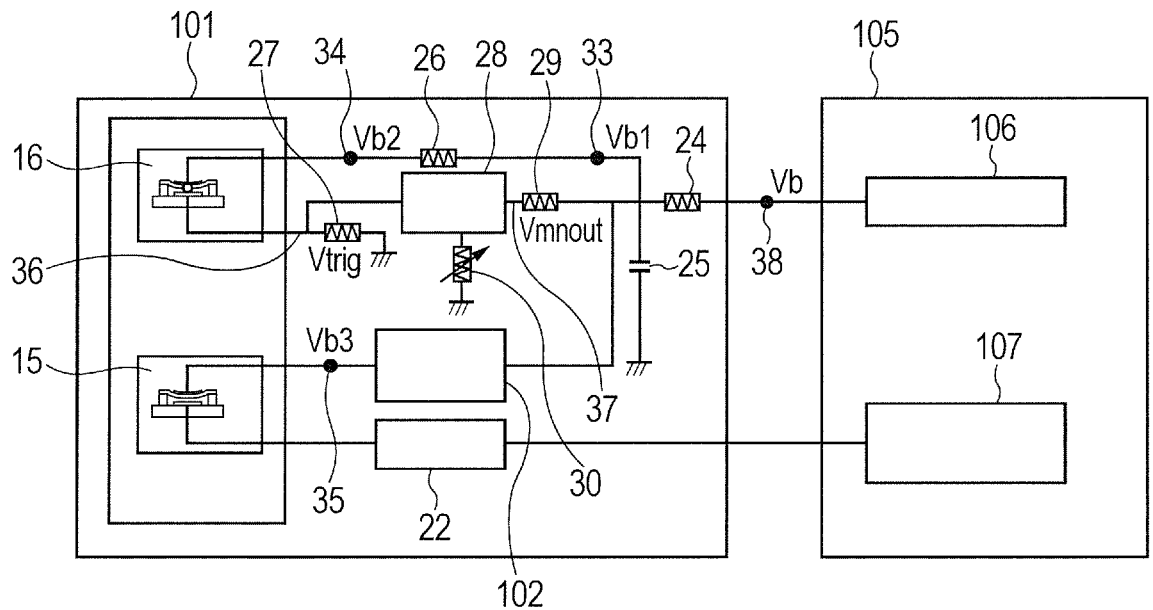

PROBE AND INFORMATION ACQUIRING DEVICE

BACKGROUND OF THE INVENTION

Field of the Invention

The present invention relates to a probe configured to perform at least one of transmission or reception (hereinafter also referred to as "transmission/reception") of an ultrasound wave such as an ultrasonic wave through use of a capacitive transducer, and to an object information acquiring device including the probe, such as an ultrasonic diagnostic apparatus. The term "ultrasound wave" is used as a term including a sound wave, an ultrasonic wave, an optical ultrasound wave, and other such waves, but in the following description, the ultrasound wave is sometimes represented by an ultrasonic wave.

Description of the Related Art

For the purpose of transmitting or receiving an ultrasonic wave, there has been proposed an ultrasonic probe using a capacitive micromachined ultrasonic transducer (CMUT), which is a capacitive ultrasonic transducer. A CMUT device requires a high and DC-potential bias voltage for maintaining a voltage across electrodes at a predetermined voltage. The CMUT device is a transducer whose electromechanical coupling coefficient changes depending on the magnitude of the bias voltage, and whose conversion characteristic increases as the bias voltage increases. When the bias voltage applied to the CMUT exceeds a certain predetermined value, displacement of a vibrating membrane of the CMUT changes drastically, and the vibrating membrane starts to be brought into contact with a substrate. This phenomenon is called "pull-in", and the bias voltage at the time when the pull-in occurs is defined as "pull-in voltage". When the phenomenon called "pull-in" occurs, the vibrating membrane and the substrate are brought into contact with each other, and the CMUT functions in a manner greatly different from what is originally expected as a transducer. The CMUT device is therefore required to be used at a bias voltage value lower than the pull-in voltage. The bias voltage value to be applied to the CMUT device is required to be determined individually for each device in consideration of a difference in pull-in voltage due to manufacturing variations and specifications that are based on an electromechanical coupling coefficient.

In an ultrasonic diagnostic apparatus disclosed in Japanese Patent No. 5303472, a memory storing a bias voltage value is mounted inside an ultrasonic probe. The ultrasonic diagnostic apparatus is configured to read the bias voltage value from the memory of the ultrasonic probe to set a value of a bias voltage to be supplied to the ultrasonic probe.

However, in the invention disclosed in Japanese Patent No. 5303472, it is required to provide, in the probe, a storage unit configured to store the bias voltage value and a communication unit and provide, in the ultrasonic diagnostic apparatus, a bias voltage control unit and a communication unit configured to communicate to/from the communication unit of the probe. Moreover, processing for controlling those units is also required.

SUMMARY OF THE INVENTION

The present invention is directed to proving a probe and an apparatus using the probe that do not require, in the probe, provision of a storage unit configured to store a bias voltage value and a communication unit and, in an apparatus main body, provision of a communication unit configured to communicate to/from the probe and a unit configured to control a bias voltage based on a value obtained by the communication.

A probe according to one aspect of the present invention includes a plurality of cells, the cell including a first electrode and a second electrode disposed so as to be opposed to the first electrode across a gap, the plurality of cells including: a first cell configured to perform at least one of transmission or reception of an ultrasound wave; and a second cell in which pull-in occurs at a voltage lower than a pull-in voltage of the first cell and which is configured to be short-circuited at a time of the pull-in.

Further features of the present invention will become apparent from the following description of exemplary embodiments with reference to the attached drawings.

BRIEF DESCRIPTION OF THE DRAWINGS

FIG. 3 is a diagram for illustrating a circuit operation of the probe according to Example 2.

FIG. 4 is a circuit block diagram for illustrating a probe and an apparatus main body according to Example 3 of the present invention.

DESCRIPTION OF THE EMBODIMENTS

In a probe according to each of examples of the present invention to be described below, a protection cell is provided in which pull-in occurs at a voltage lower than a pull-in voltage of a transmission/reception cell configured to transmit or receive an ultrasonic wave and which is configured to be short-circuited at the time of the pull-in. The pull-in occurs earlier in the protection cell to cause the protection cell to be short-circuited, to thereby prevent pull-in of the transmission/reception cell (refer to Example 1 of the present invention described later). In another mode, a bias voltage control unit including the protection cell is configured to adjust a bias voltage to be applied to the transmission/reception cell to a voltage value lower than a pull-in voltage of the transmission/reception cell (refer to Examples 2 and 3 of the present invention described later). In still another mode, an apparatus main body includes a detection unit configured to detect short-circuiting of the protection cell having the pull-in voltage lower than the pull-in voltage of the transmission/reception cell, and based on a detection result obtained by the detection unit, the bias voltage of the transmission/reception cell is adjusted to a voltage value lower than the pull-in voltage of the transmission/reception cell (refer to Example 4 of the present invention described later).

Now, examples of the present invention are described in detail with reference to the drawings, but the present invention is not limited to those examples and can be modified and changed variously within the gist thereof.

Example 1

Figure 1:
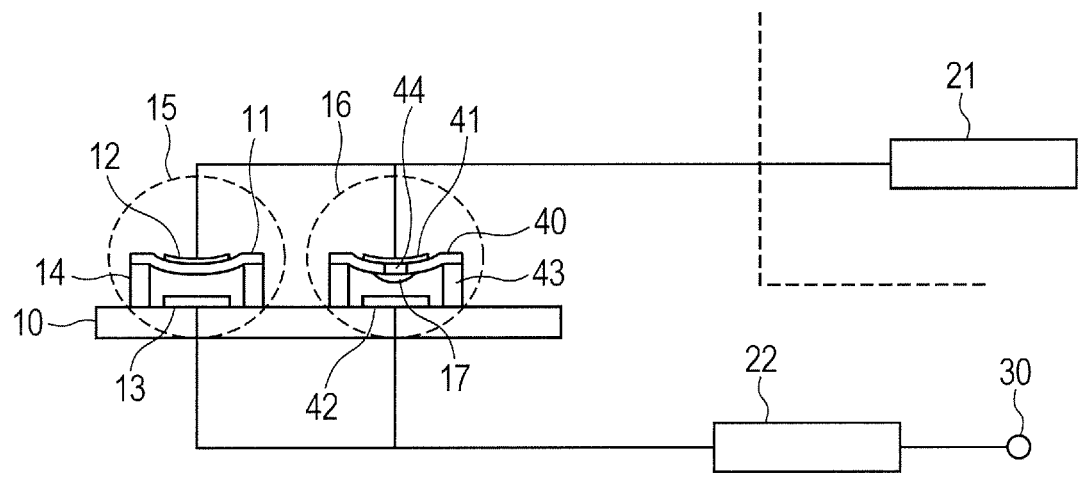
FIG. 1 is a schematic diagram for illustrating a probe according to Example 1 of the present invention.

FIG. 1 is a diagram for illustrating a probe according to Example 1. FIG. 1 is a schematic illustration of a cross section of a transmission/reception cell and a protection cell. The probe according to this example includes a transmission/reception cell 15 for ultrasonic wave transmission/reception, and a protection cell 16 in which pull-in occurs at a voltage lower than a pull-in voltage of the cell 15 for ultrasonic wave transmission/reception and which is configured to be short-circuited at the time of pull-in. Pull-in of the transmission/reception cell 15 is a phenomenon in which when a bias voltage applied thereto exceeds a certain voltage, a vibrating membrane 11 adheres to a substrate 10 side instantaneously. There is hysteresis for a voltage at which the pull-in is cancelled, and this voltage is thus lower than the pull-in voltage by a value corresponding to the hysteresis.

The transmission/reception cell 15 includes a first electrode 13 fixed on the substrate 10 shared with the protection cell 16 and a second electrode 12 disposed so as to be opposed to the first electrode 13 across a gap. The transmission/reception cell 15 has a structure in which the second electrode 12 is disposed on the vibrating membrane 11 so as to vibrate together with the vibrating membrane 11. The vibrating membrane 11 is movably supported above the substrate 10 by a support portion 14. In this example, a DC power supply circuit 21 is connected to the second electrode 12. The DC power supply circuit 21 is installed outside the probe (e.g., an apparatus main body). In the protection cell 16, a third electrode 17 is disposed on a lower surface of a vibrating membrane 40. The third electrode 17 is electrically connected to a second electrode 41 disposed on an upper surface of the vibrating membrane 40 by wiring 44 passing through the vibrating membrane 40. The protection cell 16 has the same structure as that of the transmission/reception cell 15 except for the third electrode 17 and the wiring 44. That is, also in the protection cell 16, a first electrode 42 is provided on the substrate 10, and the vibrating membrane 40 is supported above the substrate 10 by a support portion 43 in a manner that enables the vibrating membrane 40 to vibrate. In this example, the second electrode 41 of the protection cell 16 is also connected to the DC power supply circuit 21.

To the second electrode 12 of the transmission/reception cell 15, a predetermined DC voltage is applied by the DC power supply circuit 21. The first electrode 13, which is the other electrode, is connected to a transmission/reception circuit 22, and has a fixed potential around a ground (GND) potential. With this configuration, a potential difference corresponding to a bias voltage Vbias is generated between the first electrode 13 and the second electrode 12. Through application of an AC drive voltage to the first electrode 13 by the transmission/reception circuit 22, an AC component can be generated in an electrostatic attractive force acting between the first electrode and the second electrode to cause the vibrating membrane 11 to vibrate, to thereby transmit an ultrasonic wave. On the other hand, when the vibrating membrane 11 receives an ultrasonic wave to vibrate, a minute current is generated in the first electrode 13 due to electrostatic induction. In the transmission/reception circuit 22, this generated current is subjected to current-voltage conversion and the resultant voltage is amplified. In this manner, a reception signal can be extracted. An input/output terminal 30 for connection to an outside of the transmission/reception circuit 22 is connected to the main body (not shown) of the ultrasonic diagnostic apparatus. In the transmission/reception cell 15, when the bias voltage Vbias increases toward the pull-in voltage of the cell 15 to exceed a certain voltage, a phenomenon occurs in which the vibrating membrane 11 adheres to the substrate 10 side instantaneously. In the transmission/reception cell 15, a bias voltage to be used when transmitting the ultrasonic wave and a bias voltage to be used when receiving the ultrasonic wave may be the same, or may be different from each other. For example, in a reception mode, the bias voltage lower than the pull-in voltage of the protection cell 16 is applied to the transmission/reception cell 15 as a reception bias. On the other hand, in a transmission mode, a voltage lower than the reception bias is applied thereto as a transmission bias.

In the protection cell 16, a potential difference corresponding to the bias voltage Vbias is generated between the first electrode 42 and the third electrode 17. The protection cell 16 functions as a switch in which, when the voltage applied thereto reaches the pull-in voltage of the cell 16 and pull-in thus occurs, upper and lower electrodes are short-circuited and its circuit changes from an open circuit to a short circuit. The protection cell 16 is designed so that its pull-in voltage is lower than the pull-in voltage of the transmission/reception cell 15. That is, the protection cell 16 is produced by adjusting its structure by, for example, increasing an area of the cell, reducing a distance between the vibrating membrane 40 and the substrate 10, reducing elasticity of the vibrating membrane 40, and reducing a thickness of the vibrating membrane 40. The pull-in voltage of the protection cell 16 is set to, for example, from 80% to 90% of the pull-in voltage of the transmission/reception cell 15. The protection cell 16 is not used for ultrasonic wave transmission/reception, and is thus mounted at such a location that does not affect the ultrasonic wave transmission/reception by the transmission/reception cell 15.

With the above-mentioned configuration, when the bias voltage Vbias rises, the pull-in occurs earlier in the protection cell 16 than in the transmission/reception cell and the protection cell 16 is thus short-circuited because the pull-in voltage of the protection cell 16 is lower than the pull-in voltage of the transmission/reception cell 15. Thus, a voltage larger than the pull-in voltage of the protection cell 16 is never applied to the transmission/reception cell 15. In this manner, the transmission/reception cell 15 is protected. Through monitoring of an output voltage of the DC power supply circuit 21 or use of a power supply current limiter or the like, the pull-in of the protection cell 16 can be detected. In this example, the transmission/reception cell 15 and the protection cell 16 can be produced in the same process and at the same timing, and hence manufacturing variations of both of the cells can be made the same. Therefore, according to this example, through the detection of the pull-in of the protection cell 16, the bias voltage that does not cause the pull-in of the transmission/reception cell 15 can be acquired. Then, for example, in control units built into the DC power supply circuit 21 and the transmission/reception circuit 22, based on the thus detected pull-in voltage of the protection cell 16, the DC voltage of the DC power supply circuit 21 and the AC drive voltage of the transmission/reception circuit 22 are adjusted, and the transmission/reception cell 15 transmits or receives the ultrasonic wave.

In addition, even when a voltage of the pull-in voltage or higher is accidentally applied to the transmission/reception cell 15, the pull-in occurs earlier in the protection cell 16 to stop the voltage application to the transmission/reception cell 15, and hence the pull-in of the transmission/reception cell 15 can be avoided. Therefore, breakage and deterioration in characteristics of the transmission/reception cell 15 can be avoided. As another configuration, the protection cell 16 is used only for acquisition of the bias voltage that does not cause the pull-in of the transmission/reception cell 15, and the power supply to the protection cell 16 is turned off during a transmission/reception operation. As still another configuration, a DC power supply circuit other than the DC power supply circuit connected to the transmission/reception cell 15 may be additionally provided as a DC power supply circuit to be connected to the protection cell 16.

It is more desired that adjustment of the pull-in voltage of the protection cell 16 relative to the pull-in voltage of the transmission/reception cell 15 be performed by adjusting a ratio between the sizes (areas) of the vibrating membranes 11 and 40 of the respective cells. With this, only the ratio between the pull-in voltages can be set easily while the thicknesses of the respective vibrating membranes of the protection cell 16 and the transmission/reception cell 15 and the distances between the respective vibrating membranes and the substrate are kept unchanged. Further, it is more desired that the transmission/reception cell 15 and the protection cell 16 be disposed on the same substrate in proximity to each other. For example, in a configuration in which a plurality of elements each including one or more cells are disposed, the protection cell is provided for each of the elements in proximity to the element. However, it is not always required to arrange the protection cell for each of the elements, and when a set of a plurality of elements is set as one probe, it is only required to arrange one or more protection cells on the same substrate on which the plurality of elements are disposed. This is because in a region on the same substrate, manufacturing variations are substantially the same. Therefore, even when manufacturing variations occur, the ratio between the pull-in voltage of the protection cell 16 and the pull-in voltage of the transmission/reception cell 15 can be kept at a desired ratio.

Note that, in this example, the protection cell 16 is described as including the third electrode 17 on the lower surface of the vibrating membrane 40, but the present invention is not limited thereto. As long as the protection cell 16 has a configuration that enables the first electrode 42 and the second electrode 41 to be electrically connected to each other when the vibrating membrane 40 of the protection cell 16 comes in contact with the first electrode 42, such a configuration can be similarly used. For example, a configuration in which the second electrode 41 is disposed on the lower surface of the vibrating membrane 40 may also be used.

According to this example, it is not required to provide, in the probe, a bias voltage storage unit and a communication unit and provide, in the apparatus main body, a communication unit configured to communicate to/from the probe and a unit configured to control a bias voltage based on a value obtained by the communication.

Example 2

Figure 2:
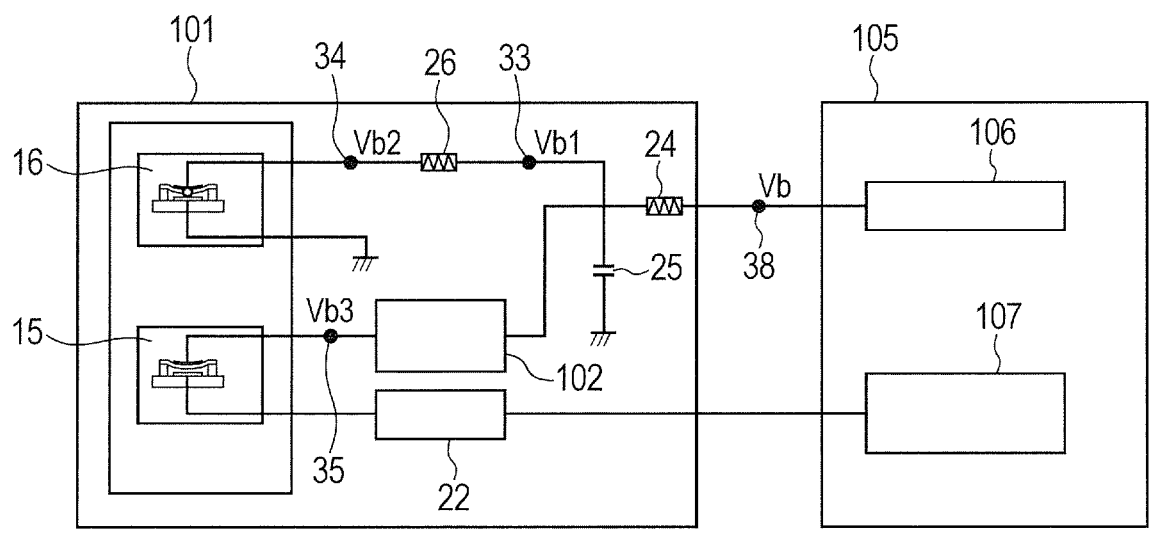
FIG. 2 is a circuit block diagram for illustrating a probe and an apparatus main body according to Example 2 of the present invention.

FIG. 2 is a circuit block diagram for illustrating a probe according to Example 2. In this example, a constant voltage output unit using the protection cell 16 is configured, and a constant voltage output is automatically applied as the bias voltage for the transmission/reception cell 15. In a configuration of this example, a probe 101 is connected to an ultrasonic diagnostic apparatus 105 that is a main body by a signal line and a bias power supply line. The signal line is involved in a function of transmitting a transmission/reception signal of the ultrasonic wave between the transmission/reception circuit 22 of the probe 101 and a transmission/reception signal processing circuit 107 of the main body. The power supply line is used to apply an output of a DC power supply circuit 106 to the electrodes of the vibrating membranes of a CMUT (the transmission/reception cell 15 and the protection cell 16). The probe 101 is detachably connected to the ultrasonic diagnostic apparatus 105 that is the main body.

To a node 38 of the probe 101, an output voltage Vb from the DC power supply circuit 106 is connected. Other connection relations are as illustrated in FIG. 2. A low-pass filter 102 is connected to a bias voltage supply unit of the transmission/reception cell 15. In this configuration, the DC voltage Vb, which is a fixed voltage, is applied to the probe 101 from the DC power supply circuit 106. Voltages at a node 33, a node 34, and a node 35 in FIG. 2 are represented by Vb1, Vb2, and Vb3, respectively. A pull-in voltage Vp of the protection cell 16 is designed to be lower than the pull-in voltage of the transmission/reception cell 15.

Changes of the voltages at the respective nodes after Vb is applied are illustrated in FIG. 3. Part (a), part (b), part (c), and part (d) of FIG. 3 are illustrations of the changes of the voltage Vb at the node 38, the voltage Vb1 at the node 33, the voltage Vb2 at the node 34, and the voltage Vb3 at the node 35, respectively. After the application of the voltage Vb, Vb1 increases during a period from t=0 to t=t1. Vb2 increases in the same manner. At t=t1, Vb2 reaches the pull-in voltage Vp of the protection cell 16. As a result, the vibrating membrane of the protection cell 16 is pulled in toward the substrate, and the upper and lower electrodes of the protection cell 16 are short-circuited. The circuit includes a capacitor 25, and hence the voltages Vb1 and Vb2 decrease depending on a time constant. When the voltage Vb2 decreases, at t=t2 (at this time, there is hysteresis as described above, and hence the voltage Vb2 is a voltage slightly lower than the pull-in voltage Vp), the protection cell 16 is opened. When the protection cell 16 is opened, because the circuit includes the capacitor 25, the voltages Vb1 and Vb2 increase depending on the time constant. When the voltage Vb2 increases, Vb2 reaches the pull-in voltage Vp of the protection cell 16, and at t=t3, the vibrating membrane of the protection cell 16 is pulled in toward the substrate again, and the upper and lower electrodes of the protection cell 16 are short-circuited. From then on, the above-mentioned operation performed from t=t1 to t=t3 is repeated. As a result, Vb1 is a voltage having Vp of the protection cell 16 as its maximum value, in which charging and discharging are repeated at fixed cycles after the application of Vb. The voltage Vb3 applied to the transmission/reception cell 15 has such a waveform as illustrated in part (d) of FIG. 3 because Vb3 exhibits only a voltage change obtained by extracting a low-frequency component of Vb1 by the low-pass filter 102. This waveform is a fixed voltage that is the pull-in voltage Vp of the protection cell 16 or lower.

According to this example, the probe 101 can be constructed with a simple circuit configuration using discrete parts such as the DC voltage circuit 106 configured to output a fixed voltage, resistors 24 and 26 inside the probe, the capacitor 25, and an inductor. It is therefore possible to provide the probe that has a simple configuration and is capable of supplying the bias voltage that does not cause the pull-in of the transmission/reception cell 15. Further, according to this example, it is possible to provide the probe that includes a bias-voltage-inside-probe control unit and that does not require, in the probe, provision of a unit configured to store a bias voltage and a communication unit and, in the main body of the ultrasonic diagnostic apparatus, provision of a bias voltage control unit, a communication unit, and a control unit therefor.

Example 3

FIG. 4 is a circuit block diagram for illustrating a probe according to Example 3. In a configuration of this example, the bias voltage is applied to the protection cell 16 via a resistance voltage dividing circuit in which a division unit is grounded with the capacitor 25, and a voltage of the division unit is applied to the transmission/reception cell 15 via the low-pass filter 102. Further, the constant voltage output unit using the protection cell 16 is provided with a monostable multivibrator 28 as an adjustable width changing unit configured to adjust a length of a period described later in which the voltage Vb1 drops, and the voltage of the division unit is adjusted based on the time constant of the monostable multivibrator.

The monostable multivibrator 28 is mounted in which a voltage change at the time of pull-in of the protection cell 16 inside the probe 101 is set as its input trigger, and other connection configurations are as illustrated in the circuit block diagram of FIG. 4. A resistor 30 is connected as a time constant adjustment resistor for generating a pulse having an arbitrary width by the monostable multivibrator 28. The monostable multivibrator 28 is set so that when a pulse waveform is input as the input trigger, its output is short-circuited for an arbitrary time period determined based on a variable time constant of the circuit. The monostable multivibrator 28 is set so as to be opened otherwise.

Figure 5:
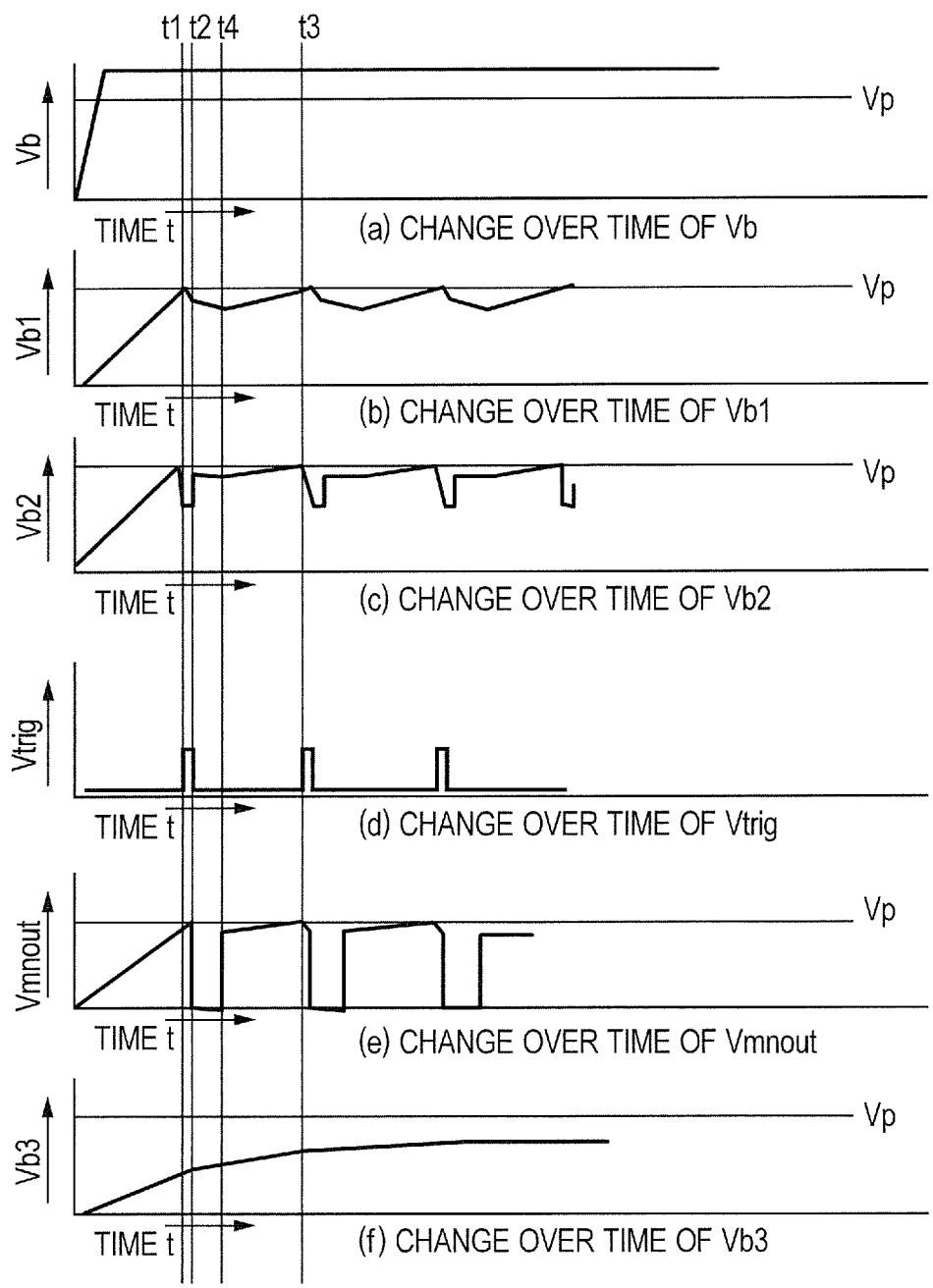
FIG. 5 is a diagram for illustrating a circuit operation of the probe according to Example 3.

Changes of voltages at respective nodes after the DC voltage Vb, which is a fixed voltage, is applied from the DC power supply circuit 106 are illustrated in FIG. 5. A voltage at a node 36, which serves as a trigger input to the monostable multivibrator 28, is represented by Vtrig, and a voltage at a node 37, which is an output voltage of the monostable multivibrator 28, is represented by Vmnout. Vmnout is applied to the division unit via a resistor 29.

The changes of the voltages at the respective nodes are illustrated in FIG. 5. Part (a), part (b), part (c), part (d), part (e), and part (f) of FIG. 5 are illustrations of the changes of the voltage Vb at the node 38, the voltage Vb1 at the node 33, the voltage Vb2 at the node 34, the voltage Vtrig at the node 36, the voltage Vmnout at the node 37, and the voltage Vb3 at the node 35, respectively. During a period from t=0 to t=t1, the voltages Vb1 and Vb2 increase after the voltage Vb is applied. At t=t1, Vb2 increases to reach the pull-in voltage Vp of the protection cell 16, and the upper and lower electrodes of the protection cell 16 are short-circuited. The value of the voltage Vb2 is a voltage obtained by dividing the voltage Vb1 with the resistor 26 and a resistor 27. When the protection cell 16 is short-circuited, Vb2 becomes the voltage Vp or lower, and hence after t=t1, the adhered vibrating membrane is separated from the substrate, and at t=t2, the protection cell 16 is opened again. During a period from t=t1 to t=t2, the voltage Vb1 decreases due to discharge from the capacitor 25. Vtrig has a pulse in which the voltage increases during the period from t=t1 to t=t2 and decreases at t2. Vtrig serves as the trigger input to the monostable multivibrator 28. In the monostable multivibrator 28, during a period from t=t2 to t=t4 determined based on the time constant of the multivibrator, its output is short-circuited, and the monostable multivibrator 28 functions to further reduce the voltage Vb1 with the discharge from the capacitor 25.

After t=t4, the capacitor 25 started to be charged because both of the protection cell 16 and the monostable multivibrator 28 are opened, and the voltage Vb1 increases. The voltage Vb2 increases along with the voltage Vb1, and then, at the time t=t3, the protection cell 16 reaches the pull-in voltage Vp, and the upper and lower electrodes are short-circuited. From then on, the operation performed from t1 to t3 is repeated. A period for reducing the voltage Vb1 is made longer, and an output value of the low-pass filter 102 can be thus made smaller than in the case of Example 2. Further, the length of the period for reducing the voltage Vb1 can be determined based on the length of the time constant of the monostable multivibrator 28, and the magnitude of the value of the voltage Vb3, which is an output of the low-pass filter 102, can be adjusted arbitrarily.

According to this example, through adjustment of the voltage of the division unit, the bias voltage of the transmission/reception cell 15 can be set lower than the pull-in voltage Vp of the protection cell 16. Further, the bias voltage of the transmission/reception cell 15 can be set arbitrarily to a voltage that does not cause pull-in. In addition, in this example, the same effects as those of Example 2 can be provided.

Example 4

Figure 6:
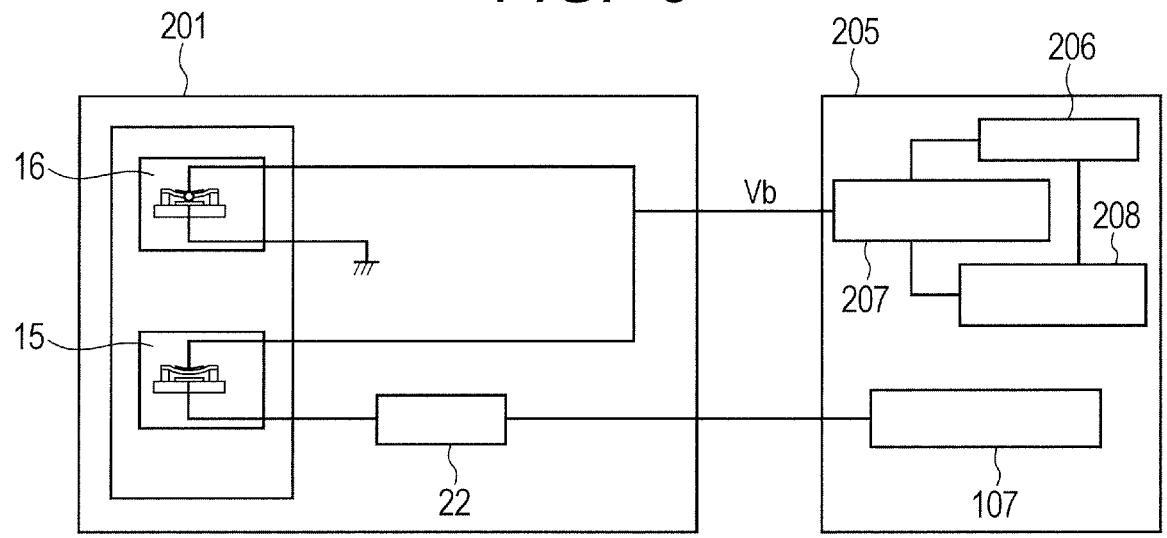
FIG. 6 is a circuit block diagram for illustrating a probe and an apparatus main body according to Example 4 of the present invention.

FIG. 6 is a diagram for illustrating a probe according to Example 4. This example relates to a probe 201 and an ultrasonic diagnostic apparatus 205, which include a detection unit configured to detect short-circuiting of the protection cell 16 (including a protection cell pull-in voltage detection circuit 207), and are configured to adjust the bias voltage of the probe to a voltage value lower than the pull-in voltage of the acoustic transmission/reception cell 15.

The ultrasonic diagnostic apparatus 205 that is the main body includes a bias voltage control circuit 206 for bias voltage supply, the protection cell pull-in voltage detection circuit 207, and a transmission/reception cell bias voltage determination circuit 208. The probe 201 includes the protection cell 16 and the transmission/reception cell 15, and is applied with the DC voltage as the bias voltage from the voltage control circuit 206. The bias voltage control circuit 206 has a voltage controlled by the bias voltage determination circuit 208. The pull-in voltage detection circuit 207 is configured to detect changes of current and voltage due to the pull-in of the protection cell 16, and notify the bias voltage determination circuit 208 of results of the detection. The bias voltage determination circuit 208 is configured to issue an instruction as to a voltage value of the bias voltage control circuit 206 based on the detection results. Further, the bias voltage determination circuit 208 is configured to perform a pull-in voltage detection sequence for detecting a pull-in voltage of the protection cell 16, store the detected pull-in voltage, and after the pull-in voltage detection sequence, issue an instruction as to an output voltage to the bias voltage control circuit 206. The pull-in voltage detection sequence is performed when, for example, the power supply to the ultrasonic diagnostic apparatus 205 is turned on or the probe 201 is connected anew to the ultrasonic diagnostic apparatus 205 that is the main body. This sequence may be started automatically, or may be started manually by an operator.

When the pull-in voltage detection sequence is stated, the bias voltage determination circuit 208 instructs the bias voltage control circuit 206 to gradually increase the bias voltage in a stepwise or continuous manner. At a moment when the bias voltage reaches the pull-in voltage of the protection cell 16 of the probe 201, the pull-in occurs in the protection cell 16. The protection cell 16 is thus brought into a short-circuit state, and the current increases. The protection cell pull-in voltage detection circuit 207 detects the current change, and sends a detection signal to the bias voltage determination circuit 208. The bias voltage determination circuit 208 stores an output voltage value of the bias voltage control circuit 206 at that time as a pull-in voltage value of the protection cell 16, and ends the pull-in voltage detection sequence. Then, based on the thus stored value, a bias voltage value to be output to the probe is determined.

After the pull-in voltage detection sequence, the bias voltage determination circuit 208 issues an instruction as to the determined value to the bias voltage control circuit 206, and the bias voltage control circuit 206 supplies an output voltage value corresponding to the determined value to the probe 201 as the bias voltage. According to this example, with only the configuration in which the protection cell 16 is provided on the probe side, the bias voltage that does not cause pull-in of the transmission/reception cell 15 can be determined automatically to be applied.

The examples described above are directed to a case where the CMUT is used as the cell for transmission and reception, but the present invention is similarly applicable to a case where the CMUT is used only for transmission or only for reception. Further, in the examples described above, it is only required that the pull-in voltage of the protection cell 16 be set lower than the pull-in voltage of the transmission/reception cell 15. In the examples described above, the DC power supply circuit 21 or 106 is connected to the second electrode 12 and the third electrode 17, and the first electrodes 13 and 42 are connected to the transmission/reception circuit 22. However, such a configuration may be similarly used that the transmission/reception circuit 22 is connected to the second electrode 12 and the third electrode 17 and the first electrodes 13 and 42 are connected to the DC power supply circuit 21 or 106. In the above description, the polarity of the bias voltage is positive, but a bias voltage of negative polarity may be similarly used.

Further, the DC power supply circuit 21 or 106 is disposed inside the ultrasonic diagnostic apparatus 105, but a DC voltage may be supplied from an external DC power supply. The protection cell 16 may be constructed with only the third electrode 17 without using the second electrode 41. The low-pass filter 102 may be constructed with, for example, a resistor and a capacitor, an inductor and a capacitor, or a resistor, an inductor, and a capacitor. Moreover, the number of low-pass filters 102 connected in stages may be one or more.

Example 5

The probe and the ultrasonic diagnostic apparatus described above in the examples including the transmission/reception cell and the protection cell are applicable to an object information acquiring device configured to use an ultrasound wave. The object information acquiring device can receive an ultrasonic wave from an object with the probe and use an electric signal output from the probe to acquire object information that reflects an optical characteristic value of the object, such as a light absorption coefficient, and object information that reflects a difference in acoustic impedance.

Figure 7A:
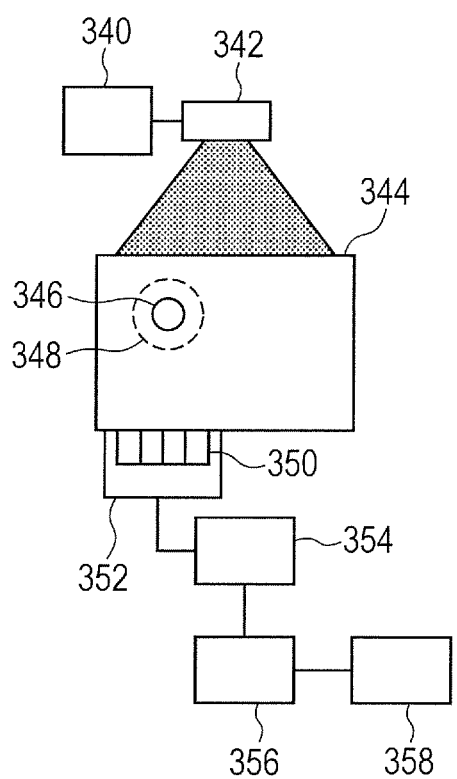
FIGS. 7A and 7B are block diagrams for illustrating an object information acquiring device according to Example 5 of the present invention.

FIG. 7A is an illustration of an object information acquiring device configured to use a photoacoustic effect. Pulsed light emitted from a light source 340 irradiates an object 344 via an optical member 342 such as a lens, a mirror, or an optical fiber. A light absorber 346 inside the object 344 absorbs energy of the pulsed light to generate a photoacoustic wave 348, which is an ultrasonic wave. A transmission/reception cell 350 inside a probe 352 receives the photoacoustic wave 348 to convert the photoacoustic wave 348 into an electric signal, and outputs the electric signal to a signal processing unit 354. The signal processing unit 354 subjects the input electric signal to signal processing such as A/D conversion and amplification, and outputs the resultant signal to a data processing unit 356. The data processing unit 356 uses the input signal to acquire object information (characteristic information that reflects an optical characteristic value of the object, such as a light absorption coefficient) as image data. Note that, herein, the signal processing unit 354 and the data processing unit 356 are collectively referred to as "processing unit", and the processing unit substantially corresponds to the transmission/reception signal processing unit 107. A display unit 358 displays an image based on the image data input from the data processing unit 356.

Figure 7B:
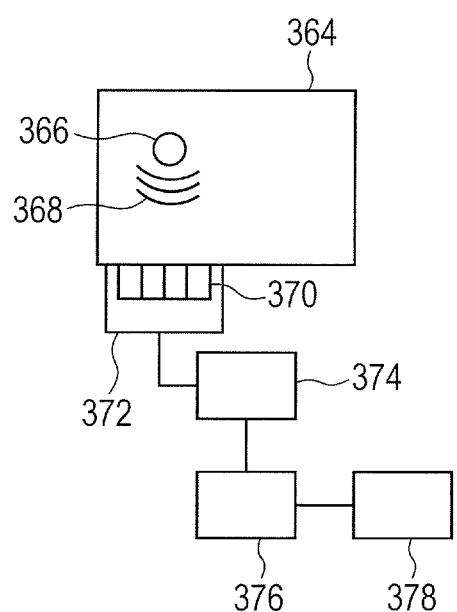

FIG. 7B is an illustration of an object information acquiring device configured to use reflection of an ultrasonic wave, such as an ultrasonic echo diagnostic apparatus. An ultrasonic wave transmitted from a transmission/reception cell 370 inside a probe 372 to an object 364 is reflected by a reflector 366. The transmission/reception cell 370 receives a reflected ultrasonic wave 368 to convert the ultrasonic wave 368 into an electric signal, and outputs the electric signal to a signal processing unit 374. The signal processing unit 374 subjects the input electric signal to signal processing such as A/D conversion and amplification, and outputs the resultant signal to a data processing unit 376. The data processing unit 376 uses the input signal to acquire object information (characteristic information that reflects a difference in acoustic impedance) as image data. A display unit 378 displays an image based on the image data input from the data processing unit 376, which includes an image forming unit configured to form an image of the object through use of at least a signal received from the transmission/reception cell.

The probe may be configured to scan mechanically, or may be configured to be moved by a user, such as a doctor or an engineer, relative to the object (handheld type). Further, in the apparatus configured to use a reflected wave as illustrated in FIG. 7B, a probe configured to transmit an ultrasonic wave may be provided separately from a probe configured to receive the ultrasonic wave.

Further, an apparatus having both of the functions of the apparatus of FIG. 7A and FIG. 7B may be adopted so as to acquire both of the object information that reflects the optical characteristic value of the object and the object information that reflects the difference in acoustic impedance. In this case, the transmission/reception cell 350 of FIG. 7A may be configured not only to receive a photoacoustic wave but also to transmit an ultrasonic wave and receive the reflected wave. Specifically, in the case of using the photoacoustic effect, the transmission/reception cell inside the probe receives the photoacoustic wave generated by the object. On the other hand, in the case of an ultrasonic echo diagnosis, the transmission/reception cell inside the probe transmits an ultrasonic wave to an object, and receives the ultrasonic wave reflected by the object.

The apparatus according to the present invention is applicable mainly to an ultrasonic diagnostic apparatus, but is also applicable to other object information acquiring devices.

According to the present invention, it is not required to provide, in the probe, a bias voltage storage unit and a communication unit and provide, in the apparatus main body, a communication unit configured to communicate to/from the probe and a unit configured to control a bias voltage based on a value obtained by the communication.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-084444, filed Apr. 16, 2015, which is hereby incorporated by reference herein in its entirety.

What is claimed is:

1. A probe, comprising a plurality of cells, each cell comprising a first electrode provided on a substrate and a second electrode disposed so as to be opposed to the first electrode across a gap,
the second electrode being provided on a vibrating membrane movably supported above the substrate by a support portion so as to vibrate together with the vibrating membrane,
the plurality of cells comprising:
a transmission/reception cell configured to perform at least one of transmission or reception of an ultrasound wave; and
a protection cell in which pull-in occurs at a voltage lower than a pull-in voltage of the transmission/reception cell and which is configured to be short-circuited when the pull-in occurs,
wherein the protection cell further comprises a third electrode provided on a surface of the vibrating membrane that is opposed to the first electrode,
wherein the second electrode is disposed on a surface of the vibrating membrane that is opposite to the surface on which the third electrode is disposed, and
wherein the short circuit occurs by contact of the first electrode and the third electrode.

2. The probe according to claim 1, further comprising a bias voltage control unit,
wherein the bias voltage control unit is configured to automatically adjust, through use of short-circuiting of the protection cell, a bias voltage to be applied to the transmission/reception cell to a voltage value lower than the pull-in voltage of the transmission/reception cell.

3. The probe according to claim 2, wherein the bias voltage control unit is configured to apply a predetermined DC voltage to the protection cell via a resistance voltage dividing circuit in which a division unit to be applied with the predetermined DC voltage is grounded with a capacitor, and apply a voltage of the division unit to the transmission/reception cell via a low-pass filter.

4. The probe according to claim 3, wherein the bias voltage control unit is configured to adjust the voltage of the division unit based on a time constant of a monostable multivibrator.

5. The probe according to claim 1, wherein a bias voltage to be applied to the transmission/reception cell is adjusted to a voltage value lower than the pull-in voltage of the transmission/reception cell based on a detection result obtained by a detection unit of an apparatus main body, the detection unit being configured to detect short-circuiting of the protection cell.

6. The probe according to claim 1, wherein the transmission/reception cell and the protection cell are electrically connected to a common DC power supply circuit.

7. The probe according to claim 1, wherein adjustment of a pull-in voltage of the protection cell relative to the pull-in voltage of the transmission/reception cell is performed by adjusting a ratio between areas of the vibrating membrane of the transmission/reception cell and the vibrating membrane of the protection cell.

8. The probe according to claim 1, wherein the transmission/reception cell and the protection cell are disposed on the same substrate.

9. An ultrasonic diagnostic apparatus, comprising:
the probe according to claim 1; and
an apparatus main body to which the probe is to be detachably connected.

10. An information acquiring device, comprising:
a probe configured to receive an ultrasound wave from an object to convert the ultrasound wave into an electric signal; and
a processing unit configured to acquire information on the object through use of the electric signal from the probe,
wherein the probe comprises the probe according to claim 1.

11. The information acquiring device according to claim 10,
wherein the probe is configured to transmit an ultrasound wave from the probe to the object, and receive the ultrasound wave reflected by the object.

12. The information acquiring device according to claim 10, wherein the probe is configured to receive the ultrasound wave, which is generated by irradiating the object with light.

13. The information acquiring device according to claim 12, further comprising a light source configured to irradiate the object with the light.

14. The information acquiring device according to claim 10, wherein the processing unit comprises a display that forms an image of the object through use of at least a signal received from the transmission/reception cell.

15. The probe according to claim 1, wherein the second electrode and the third electrode are electrically connected to each other by through wiring passing through the vibrating membrane.

16. A probe comprising:
a plurality of cells, each cell comprising a first electrode provided on a substrate and a second electrode disposed so as to be opposed to the first electrode across a gap, the second electrode being provided on a vibrating membrane movably supported above the substrate by a support portion so as to vibrate together with the vibrating membrane; and
a bias voltage control unit; wherein the plurality of cells comprises:
a transmission/reception cell configured to perform at least one of transmission and reception of an ultrasound wave; and
a protection cell in which pull-in occurs at a voltage lower than a pull-in voltage of the transmission/reception cell and which is configured to be short-circuited when the pull-in occurs,
wherein the bias voltage control unit is configured to automatically adjust, through use of short-circuiting of the protection cell, a bias voltage to be applied to the transmission/reception cell to a voltage value lower than the pull-in voltage of the transmission/reception cell, wherein the protection cell further comprises a third electrode provided on a surface of the vibrating membrane that is opposed to the first electrode, wherein the second electrode is disposed on a surface of the vibrating membrane that is opposite to the surface on which the third electrode is disposed, and wherein the short circuit occurs by contact of the first electrode and the third electrode.

17. The probe according to claim 16, wherein the bias voltage control unit is configured to apply a predetermined DC voltage to the protection cell via a resistance voltage dividing circuit in which a division unit to be applied with the predetermined DC voltage is grounded with a capacitor, and apply a voltage of the division unit to the transmission/reception cell via a low-pass filter.

18. An ultrasonic diagnostic apparatus, comprising:
the probe according to claim 16; and
an apparatus main body to which the probe is to be detachably connected.

19. An information acquiring device, comprising:
the probe according to claim 16, which receives the ultrasound wave from an object and converts the ultrasound wave into an electric signal; and
a processing unit configured to acquire information on the object through use of the electric signal from the probe.

\* \* \* \* \*